United States Patent [19]
Rodak

[11] Patent Number: 5,470,008
[45] Date of Patent: Nov. 28, 1995

[54] APPARATUS FOR APPLYING SURGICAL FASTENERS

[75] Inventor: Daniel P. Rodak, Milford, Conn.

[73] Assignee: United States Surgical Corporation, Norwalk, Conn.

[21] Appl. No.: 170,556

[22] Filed: Dec. 20, 1993

[51] Int. Cl.⁶ .................................................. A61B 17/072
[52] U.S. Cl. .............................. 227/176; 227/19; 227/178
[58] Field of Search ............................. 227/19, 175, 176, 227/177, 178, 180

[56] References Cited

U.S. PATENT DOCUMENTS

| | | |
|---|---|---|
| D. 283,733 | 5/1986 | Rawson et al. . |
| 3,079,606 | 3/1963 | Bobrov et al. . |
| 3,490,675 | 1/1970 | Green et al. . |
| 3,494,533 | 2/1970 | Green et al. . |
| 3,499,591 | 3/1970 | Green . |
| 3,692,224 | 9/1972 | Astafiev et al. . |
| 3,795,034 | 3/1974 | Strekopytov et al. . |
| 4,086,926 | 5/1978 | Green et al. . |
| 4,296,881 | 10/1981 | Lee . |
| 4,305,539 | 12/1981 | Korolkov et al. . |
| 4,354,628 | 10/1982 | Green . |
| 4,383,634 | 5/1983 | Green . |
| 4,415,112 | 11/1983 | Green . |
| 4,429,695 | 2/1984 | Green . |
| 4,442,964 | 4/1984 | Becht . |
| 4,508,253 | 4/1985 | Green . |
| 4,520,817 | 6/1985 | Green . |
| 4,527,724 | 7/1985 | Chow et al. . |
| 4,530,453 | 7/1985 | Green . |
| 4,568,009 | 2/1986 | Green . |
| 4,589,582 | 5/1986 | Bilotti . |
| 4,591,085 | 5/1986 | Di Giovanni . |
| 4,605,004 | 8/1986 | Di Giovanni et al. . |
| 4,606,344 | 8/1986 | Di Giovanni . |
| 4,606,345 | 8/1986 | Dorband et al. . |
| 4,607,636 | 8/1986 | Kula et al. . |
| 4,608,981 | 9/1986 | Rothfuss et al. . |
| 4,633,861 | 1/1987 | Chow et al. . |
| 4,633,874 | 1/1987 | Chow et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,863,088 | 9/1989 | Redmond et al. . |
| 4,869,415 | 9/1989 | Fox . |
| 4,881,544 | 11/1989 | Green et al. . |
| 4,881,545 | 11/1989 | Isaacs et al. . |
| 4,892,244 | 1/1990 | Fox et al. . |
| 4,915,100 | 4/1990 | Green . |
| 4,938,408 | 7/1990 | Bedi et al. . |
| 4,941,623 | 7/1990 | Pruitt . |
| 4,955,959 | 9/1990 | Tompkins et al. . |
| 5,031,814 | 7/1991 | Tompkins et al. . |
| 5,065,929 | 11/1991 | Schulze et al. . |
| 5,071,052 | 12/1991 | Rodak et al. . |
| 5,074,454 | 12/1991 | Peters . |
| 5,083,695 | 1/1992 | Foslien et al. . |
| 5,100,042 | 3/1992 | Gravener et al. . |
| 5,106,008 | 4/1992 | Tompkins et al. . |
| 5,129,570 | 7/1992 | Schulze et al. . |

FOREIGN PATENT DOCUMENTS

| | | |
|---|---|---|
| 5476486 | 9/1986 | Australia . |
| 5476586 | 9/1986 | Australia . |
| 0324638 | 7/1989 | European Pat. Off. . |
| 0373762 | 6/1990 | European Pat. Off. . |
| 0380025 | 8/1990 | European Pat. Off. . |
| 0489436 | 6/1992 | European Pat. Off. . |
| 8302247 | 7/1983 | WIPO . |

Primary Examiner—Rinaldi I. Rada

[57]  ABSTRACT

An apparatus is provided for applying a plurality of surgical fasteners to body tissue. The apparatus includes a staple carrying cartridge having an internal lockout mechanism for preventing operation of the apparatus after the staples have been fired from the cartridge. The lockout mechanism is movable between a first position prior to a staple firing operation wherein a firing mechanism is permitted to enter the staple cartridge and a second position upon retraction of the firing mechanism from the staple cartridge following a staple firing operation wherein the firing mechanism is prevented from entering the staple cartridge.

3 Claims, 17 Drawing Sheets

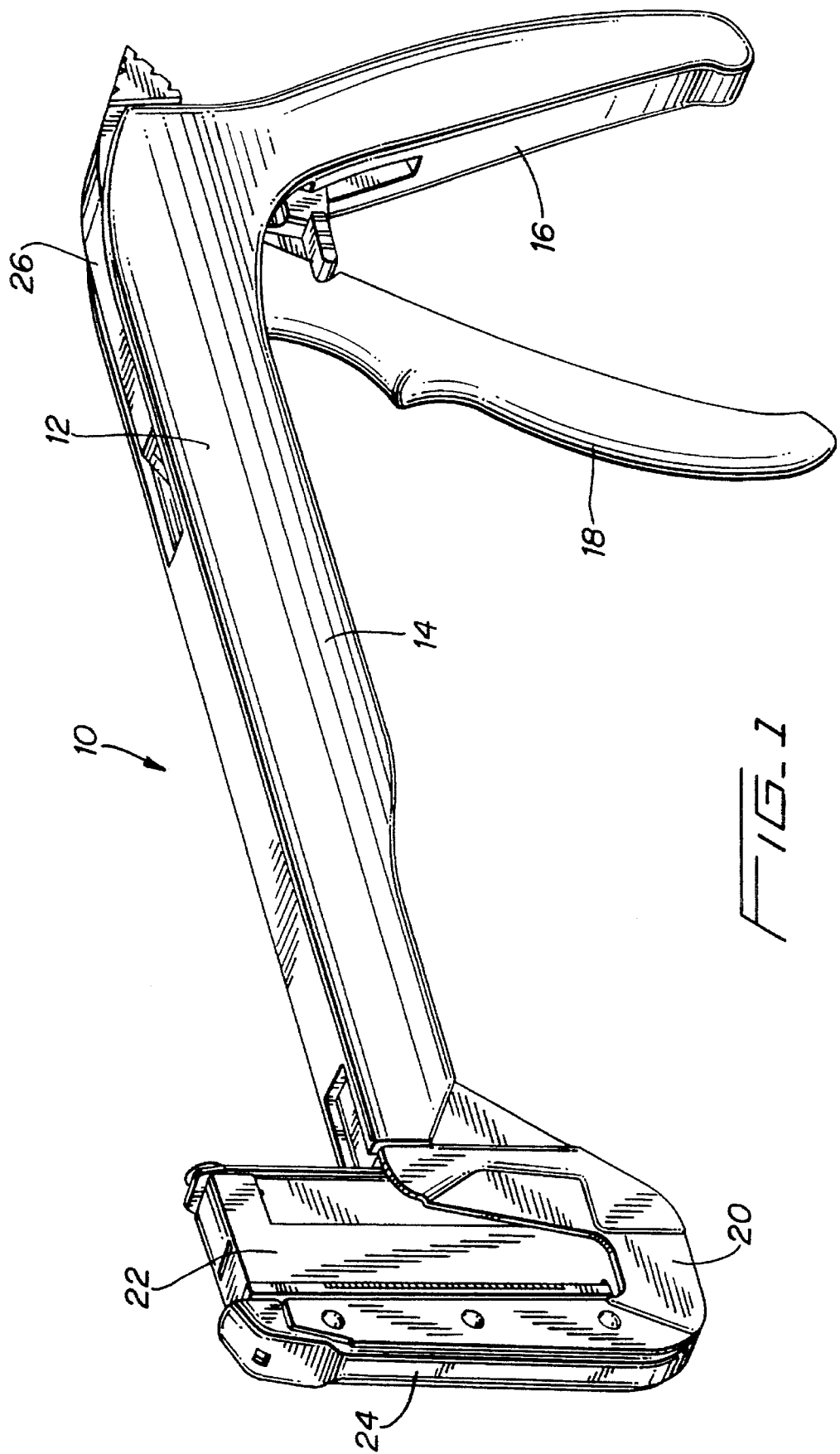
FIG_1

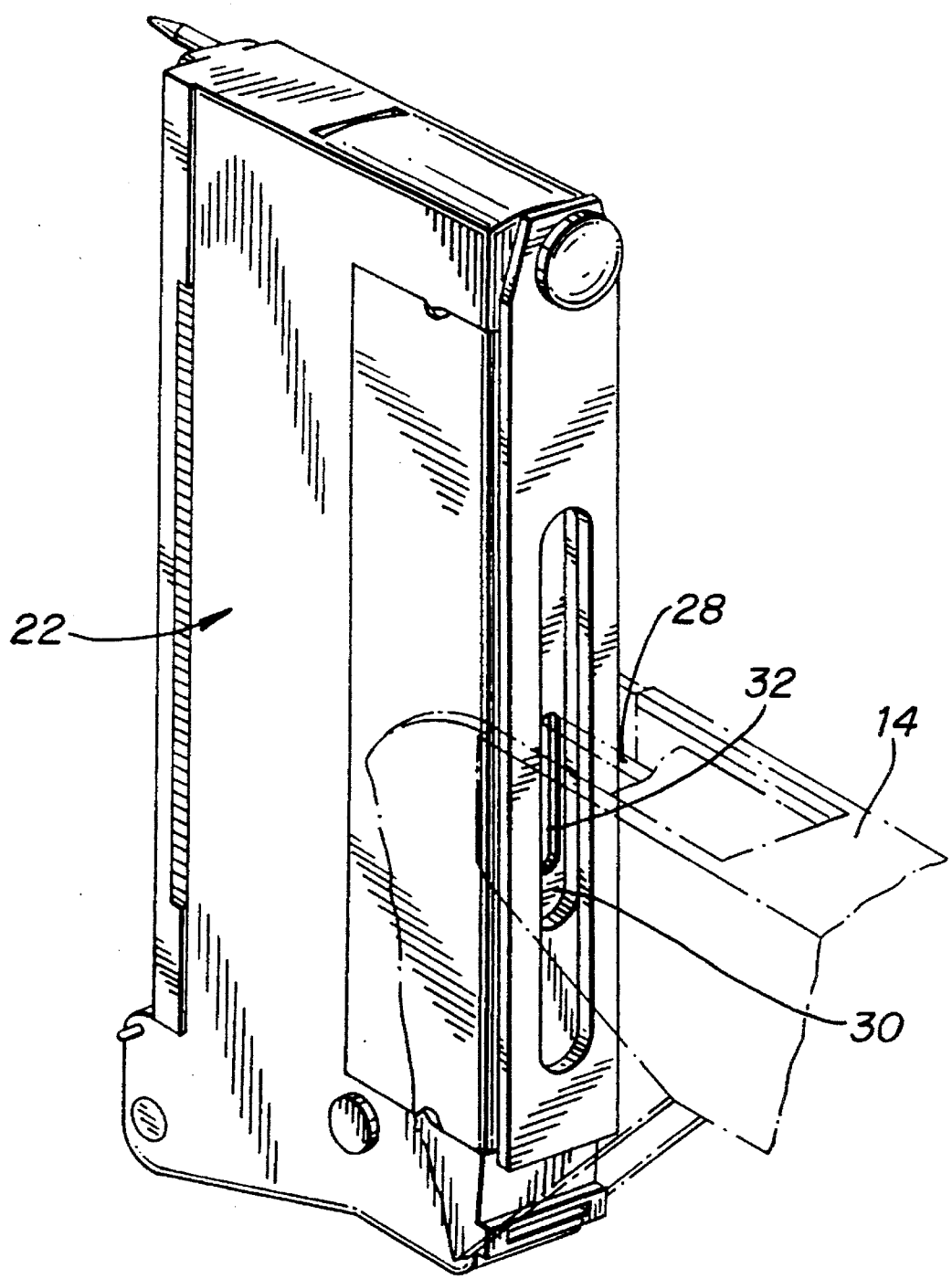

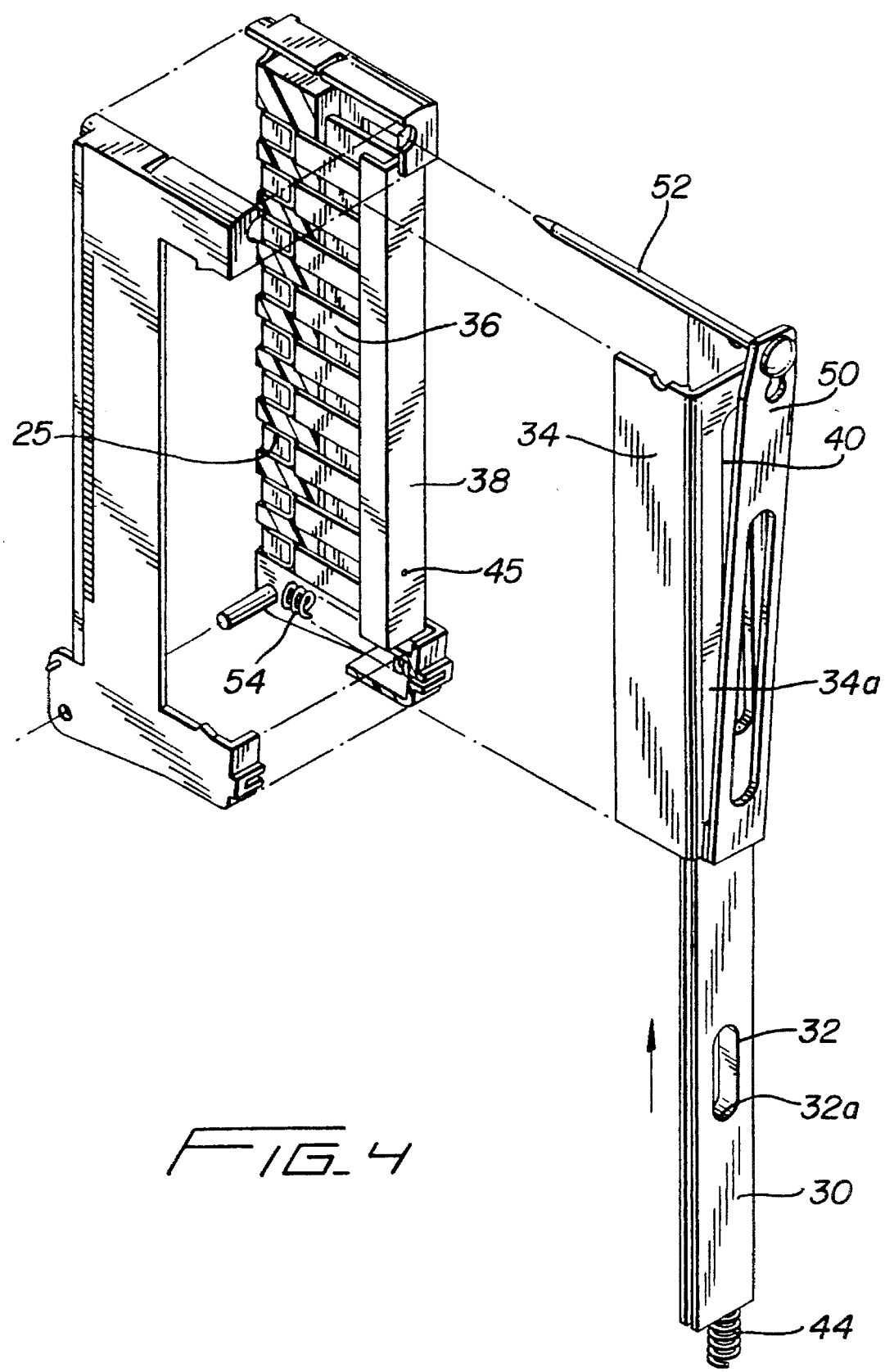

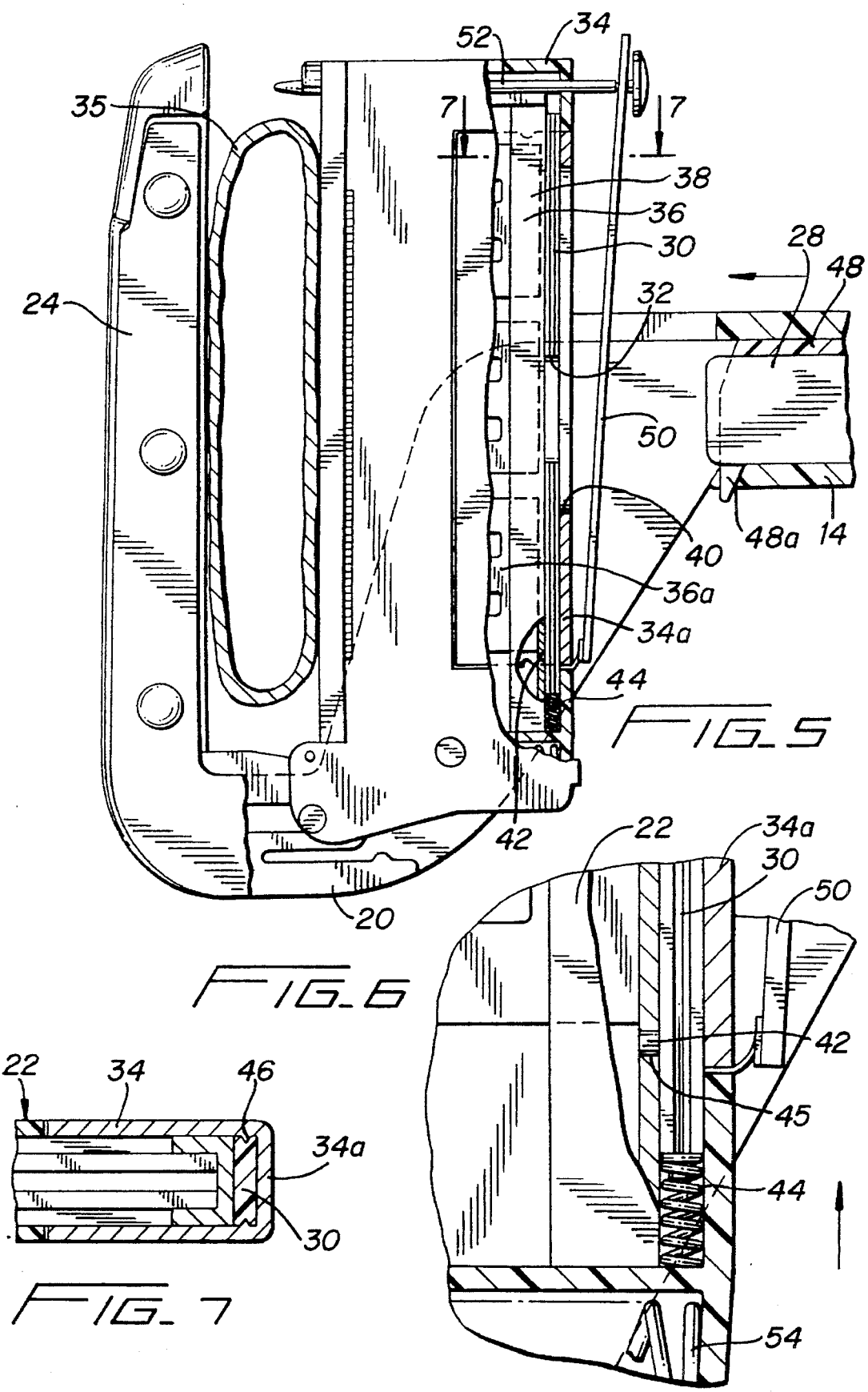

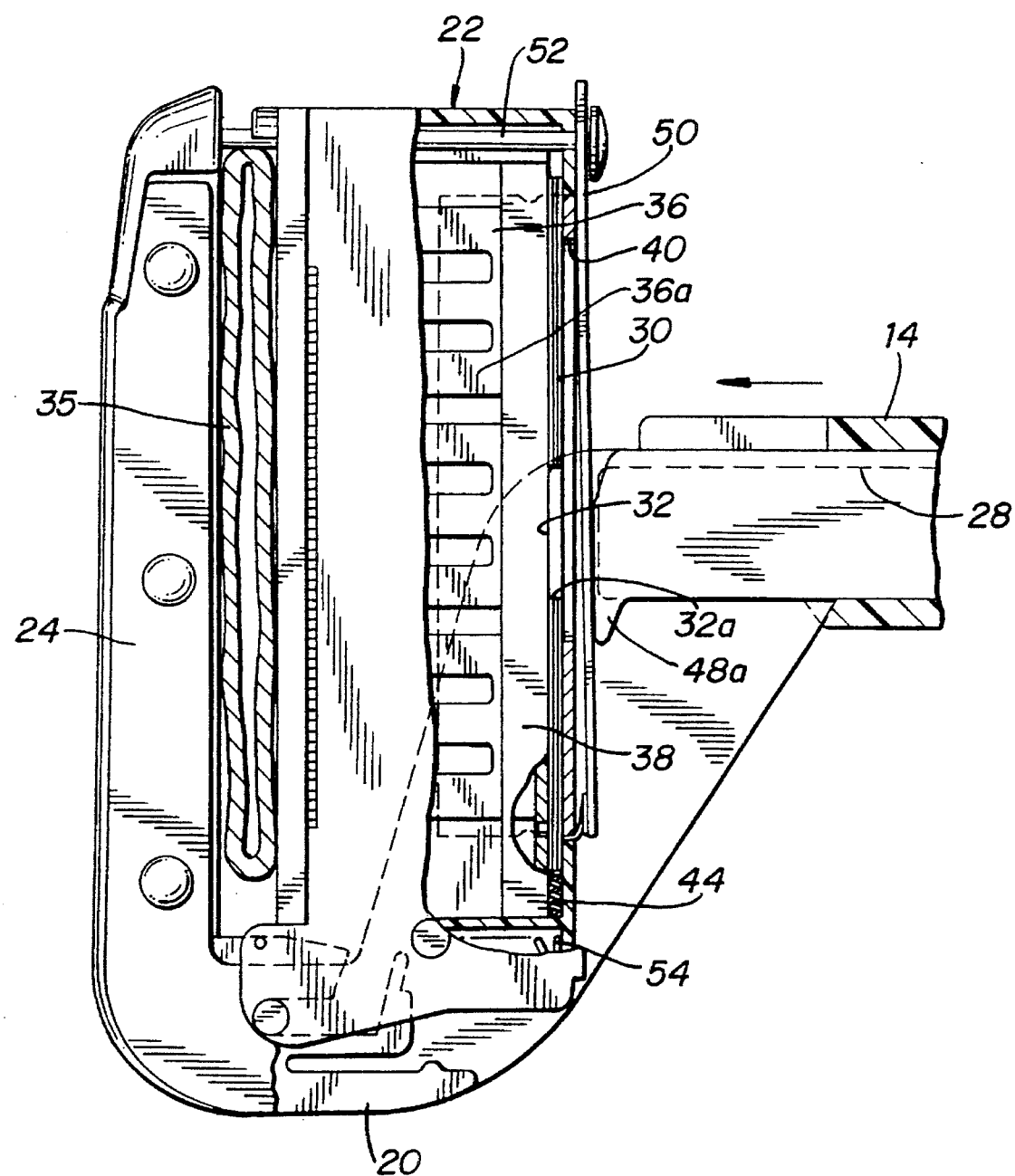

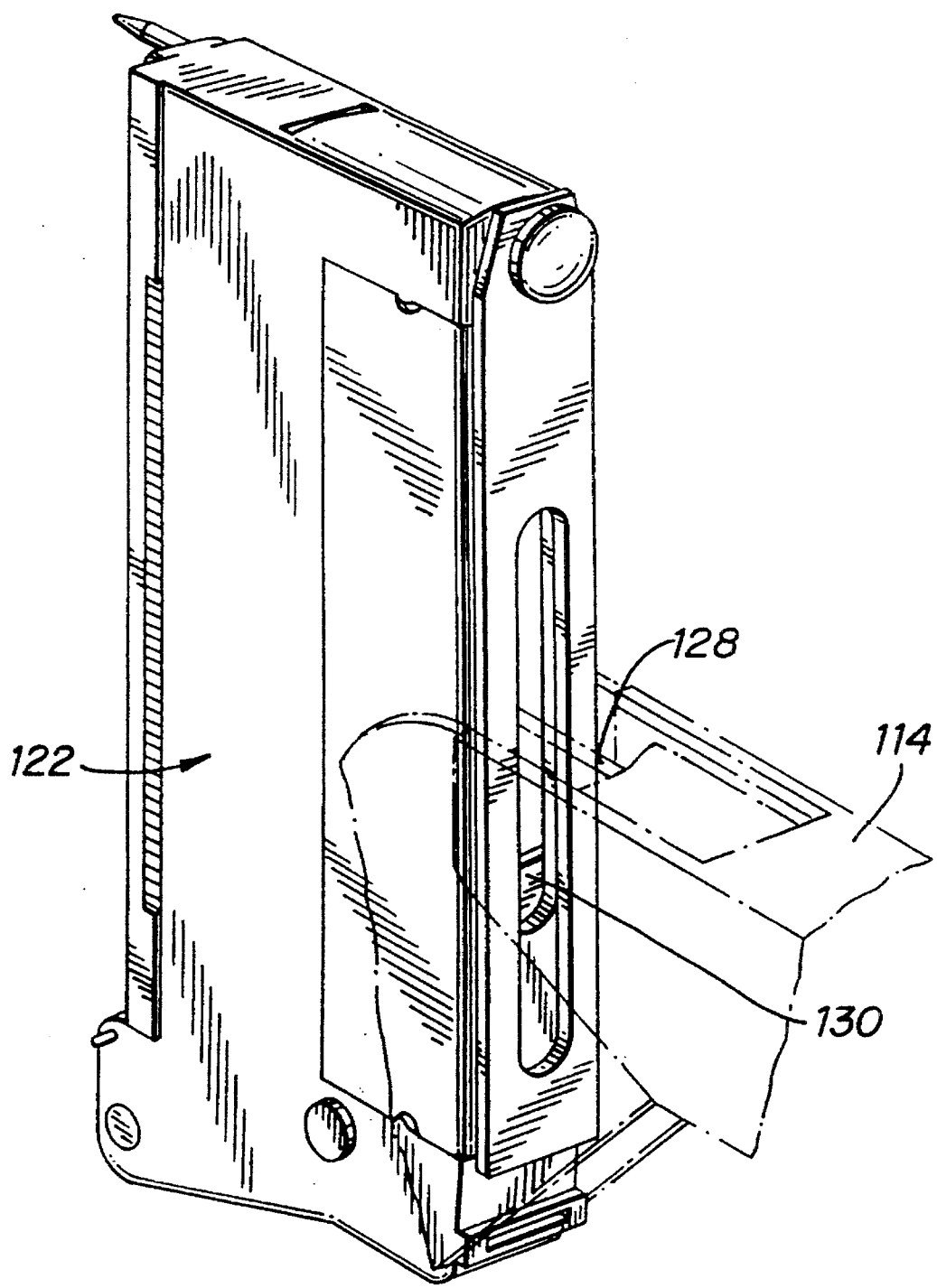
FIG_16

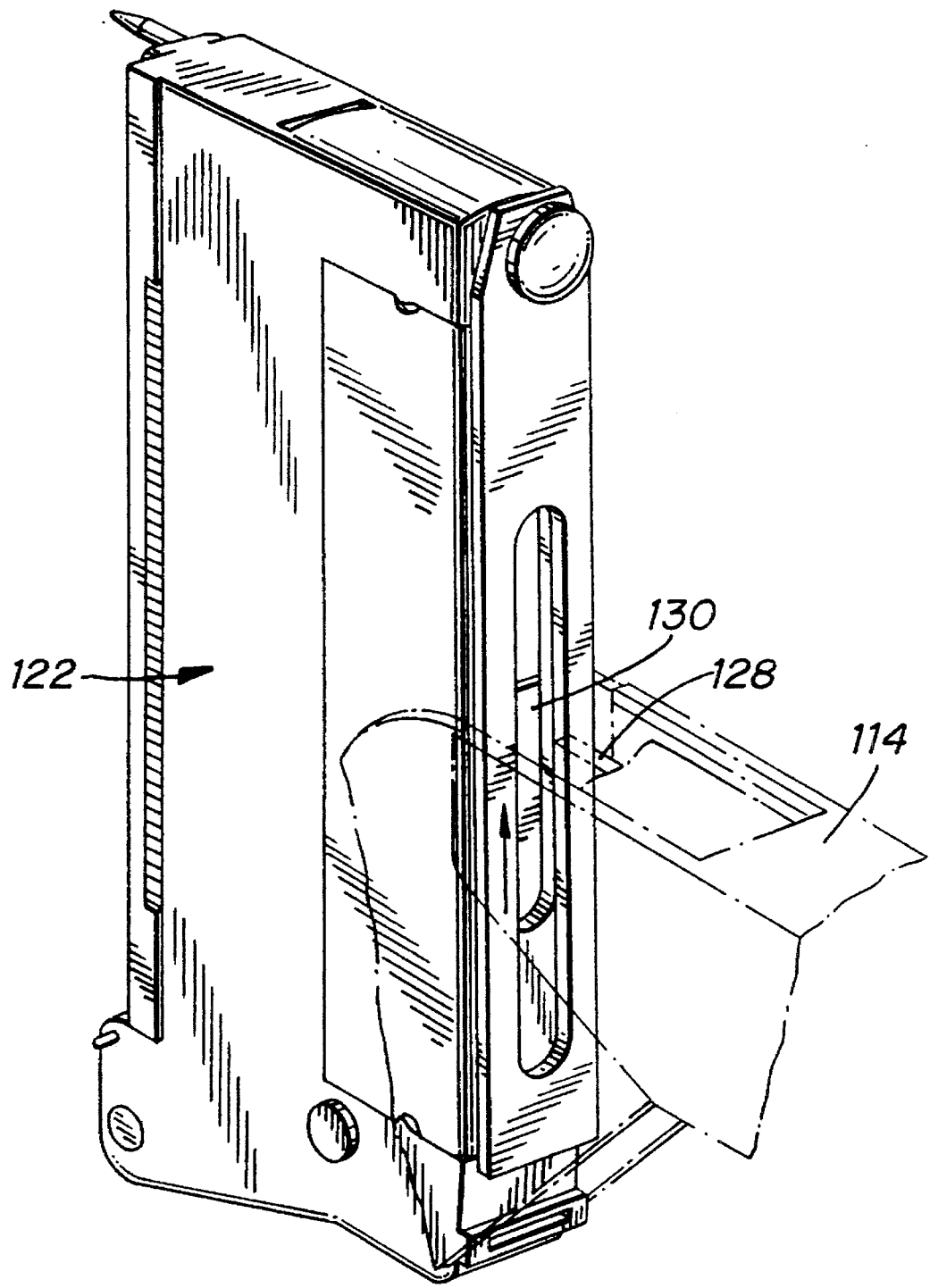

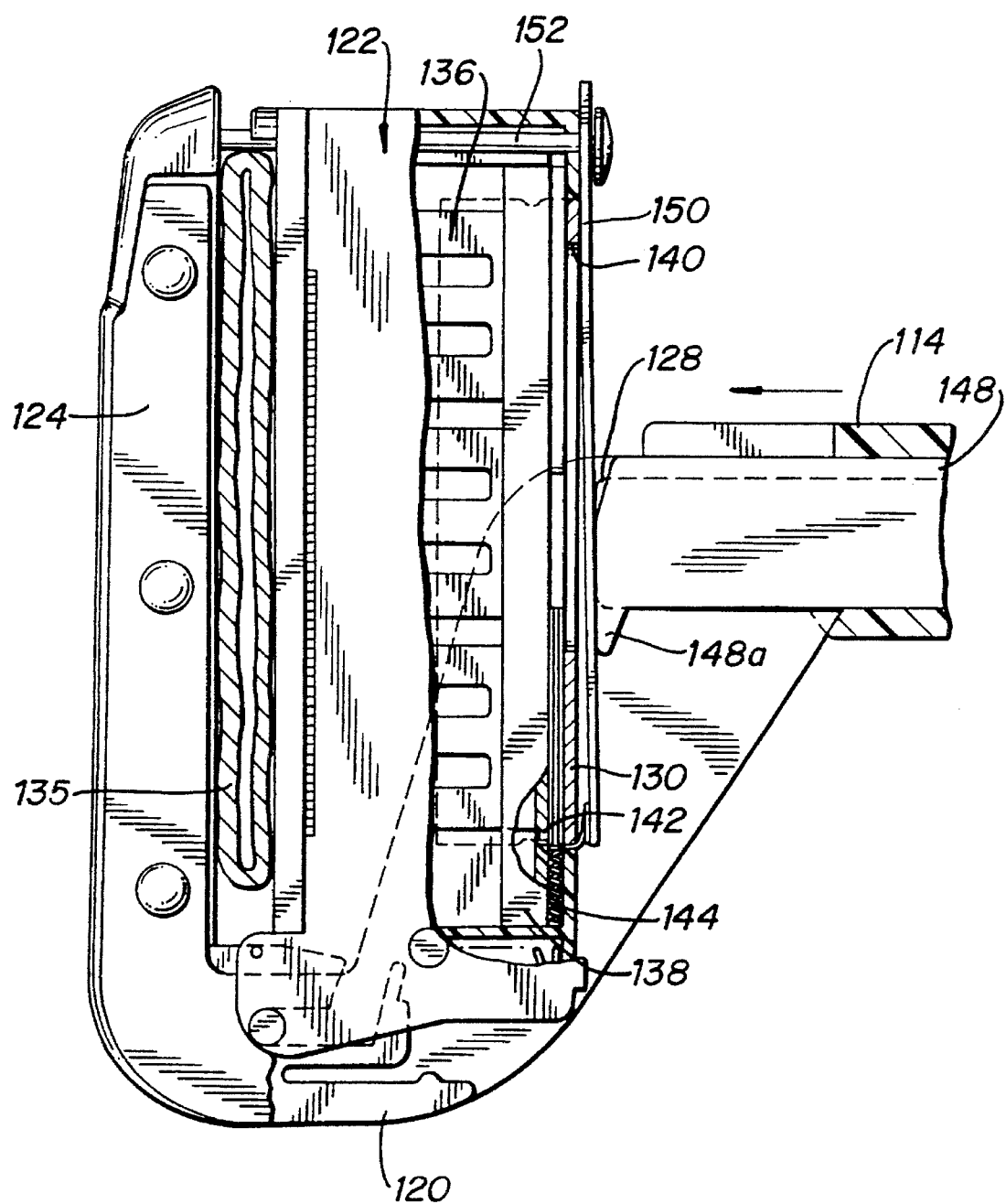

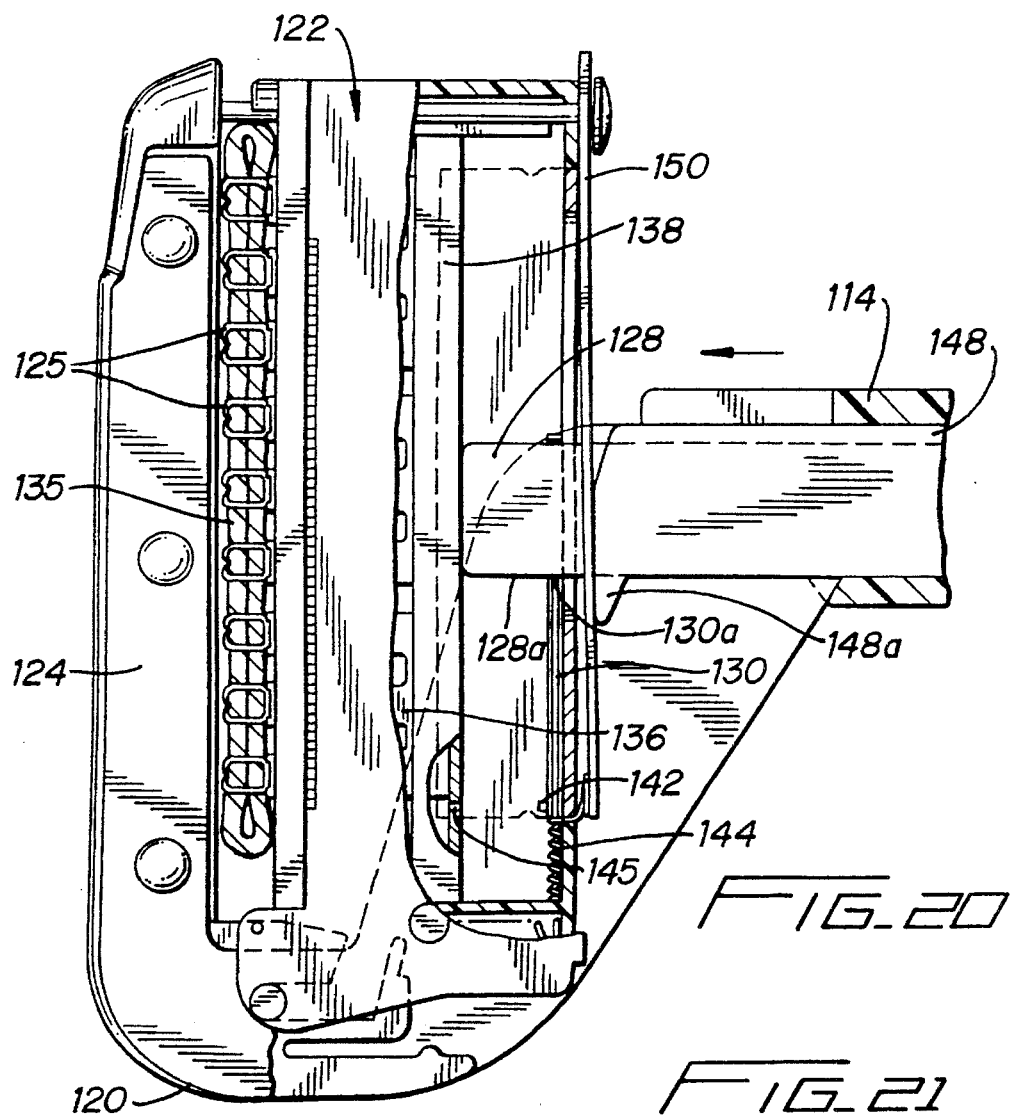
FIG_20
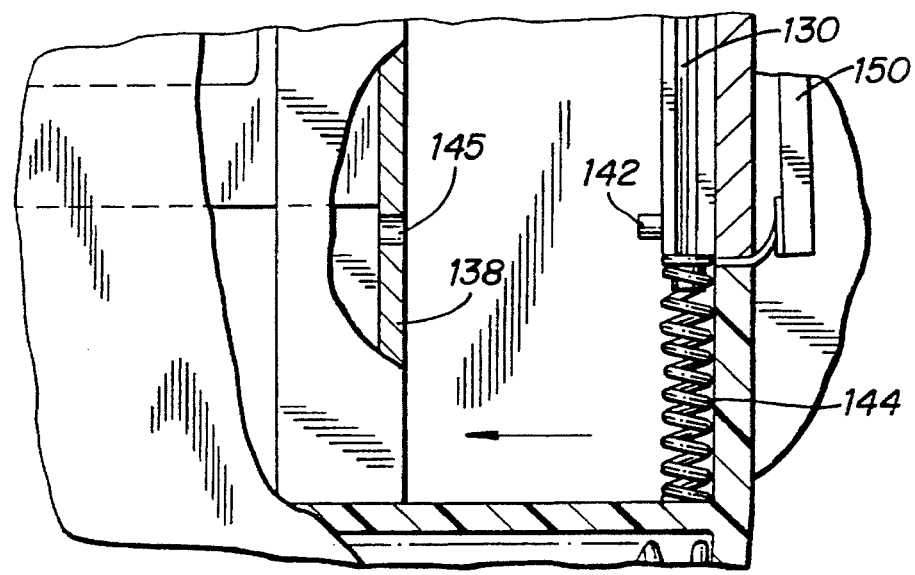
FIG_21

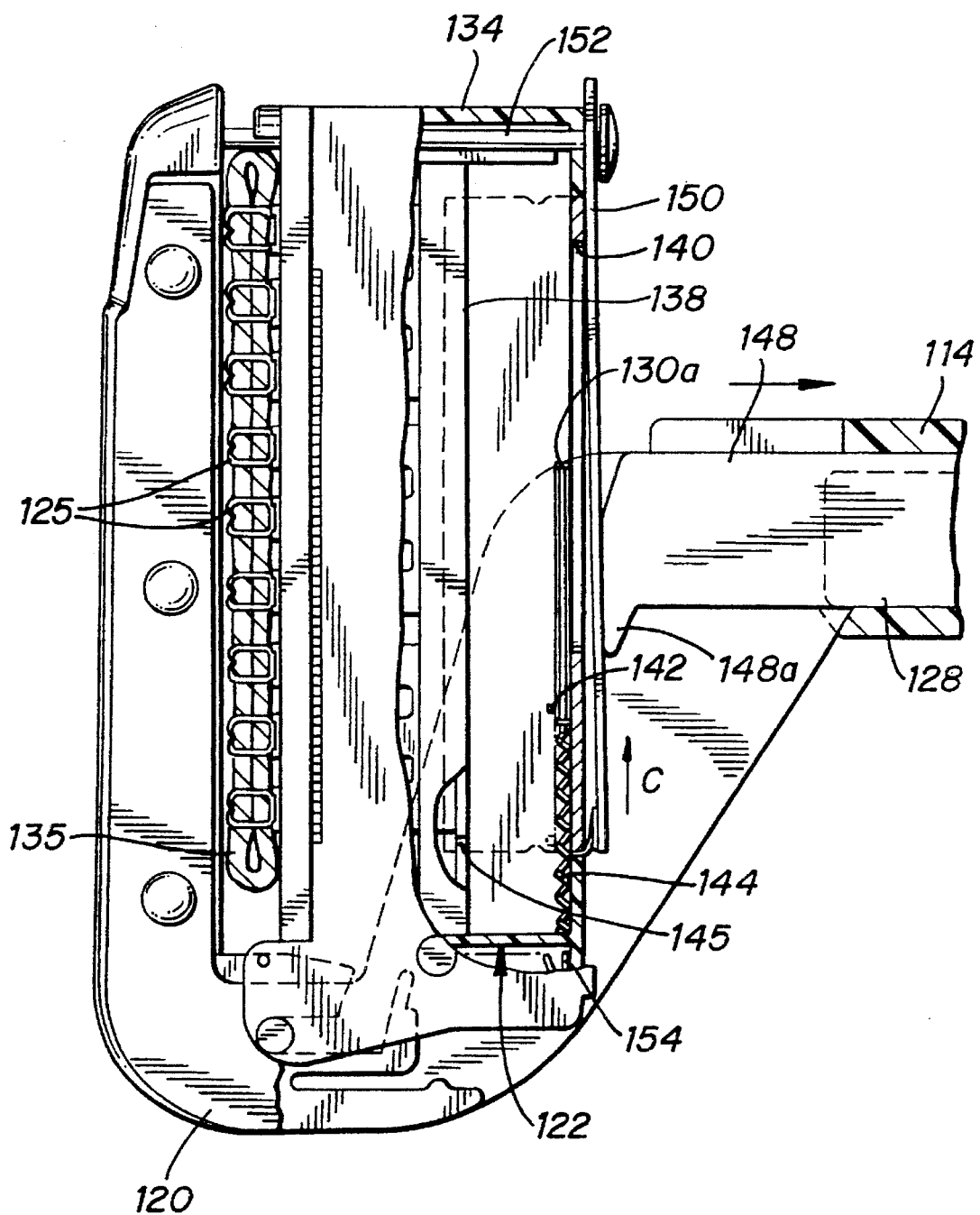

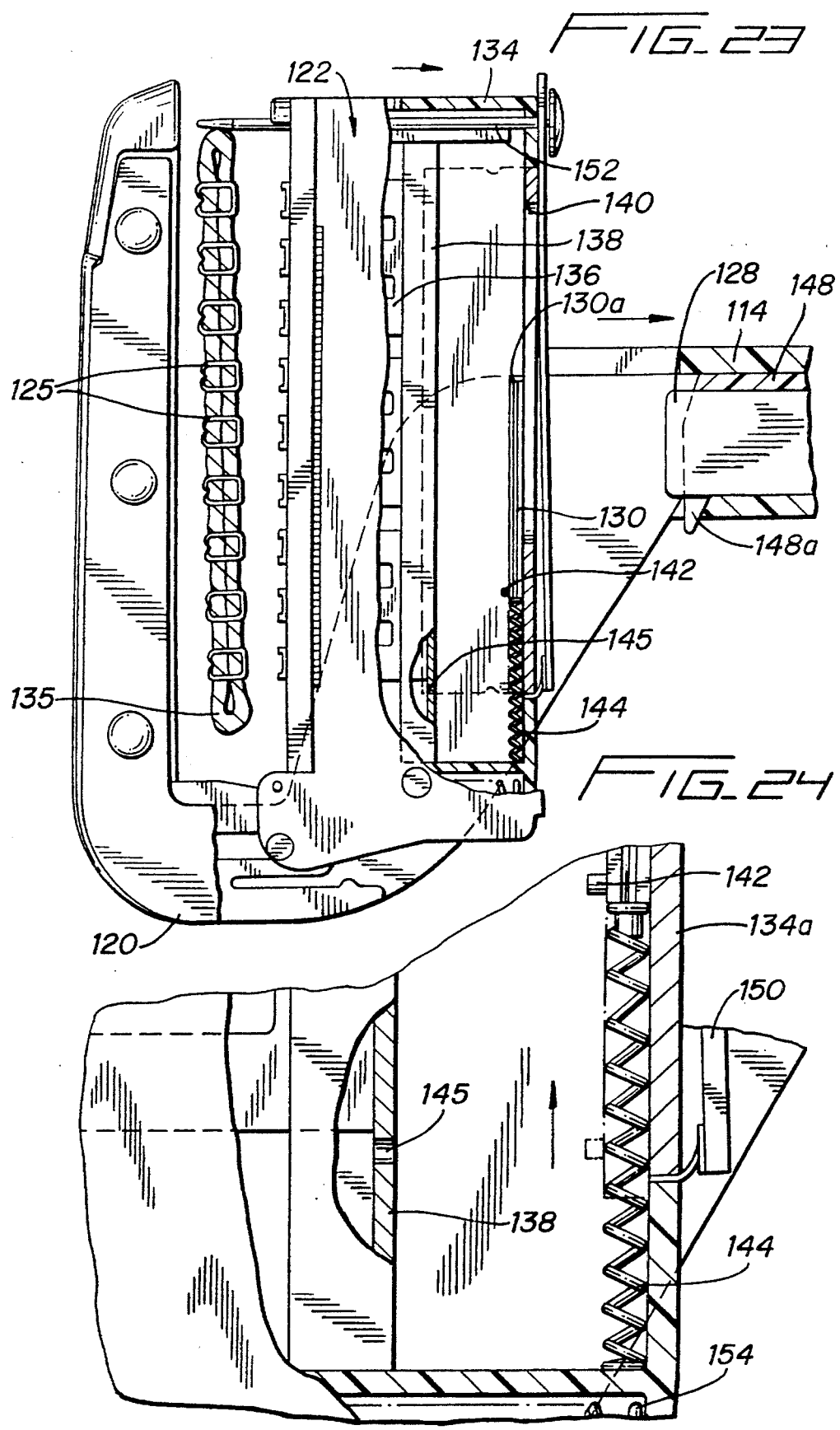

APPARATUS FOR APPLYING SURGICAL FASTENERS

BACKGROUND OF THE INVENTION

1. Field of the Invention

This invention relates to an apparatus for applying a plurality of surgical fasteners to body tissue, and more particularly, to a surgical stapler including a staple cartridge assembly having a lockout mechanism for preventing refiring of the apparatus after the staples have been ejected from the cartridge.

2. Description of the Related Art

Surgical stapling apparatus for simultaneously applying a plurality of surgical fasteners to body tissue are well known in the art. Typically these apparatus include a fastener holder disposed on one side of the tissue to be fastened, an anvil assembly substantially parallel to the fastener holder on the other side of the tissue to be fastened, a mechanism for linearly translating the fastener holder and the anvil assembly toward one another so that the tissue is clamped therebetween, and a mechanism for driving the fasteners from the fastener holder so that the ends of the fasteners pass through the tissue and form finished fasteners as they make contact with the anvil assembly, thereby producing an array of finished fasteners in the tissue.

In common use are devices such as those disclosed in U.S. Pat. Nos. 4,354,628 and 4,665,916. More particularly, U.S. Pat. No. 4,354,628 discloses a surgical stapler apparatus for forming an array of surgical staples in body tissue including an anvil member against which the staplers are crimped, and a staple holder pivotally mounted adjacent one end of the anvil member.

U.S. Pat. No. 4,665,916 discloses a surgical stapling apparatus comprising an anvil assembly against which fasteners are formed and a fastener holder pivotally mounted adjacent one end of the anvil assembly, a spacer member at the other end so constructed to displace tissue that would otherwise obstruct the spacer member from properly positioning the fastener holder relative to the anvil assembly to insure proper fastener formation, and a knife assembly to cut the tissue between the rows of formed fasteners.

In use, a surgeon selects the body tissue to be fastened, positions the instrument so that the tissue is between the anvil assembly and the fastener holder (or cartridge), then actuates the stapler. In some surgical applications, it is necessary to perform several stapling tasks and thus it is not uncommon for a surgeon to replace the cartridge several times during such procedures. In the course of an operation, however, a surgeon or nurse may, inadvertently try to reuse the apparatus with a spent cartridge in the apparatus or select a spent cartridge for placement into the apparatus. In such an instance, operation of the apparatus would be ineffective and would result in a prolongation of the procedure.

SUMMARY OF THE INVENTION

The present invention provides a surgical stapler comprising a frame having a longitudinal axis and a cartridge receiving portion, an anvil portion positioned at a distal end of the frame, and a cartridge containing a plurality of fasteners, a plurality of fastener drivers and a fastener driving plate positioned proximally of said fastener drivers. The cartridge is mountable in the cartridge receiving portion. The stapler further includes means for moving said cartridge between a proximal first position and a distal second position closer to said anvil portion and means for substantially simultaneously firing the fasteners from the cartridge in a direction substantially parallel to the longitudinal axis, the firing means including a firing shaft and the fastener driving plate. A slidable plate is positioned in the cartridge proximally of the fastener drivers and substantially perpendicular to the longitudinal axis. The slidable plate is spring biased towards the firing shaft and has an elongated aperture dimensioned and configured to allow passage of the firing shaft therethrough. A retaining pin extends from the slidable plate for reception in an opening in the fastener driving plate. The slidable plate is movable from a first position wherein the retaining pin is positioned in the opening to a second position wherein the retaining pin is released from the opening after distal movement of the firing shaft and the driving plate to fire the fasteners and retraction of the firing shaft, wherein in the second position at least a portion of the elongated aperture is out of alignment with the firing shaft such that passage of the firing shaft is prevented by the slidable plate.

Further features of the surgical stapler of the subject invention will become more readily apparent to those having ordinary skill in the art to which this invention appertains from the following detailed description of the invention taken in conjunction with the drawings.

BRIEF DESCRIPTION OF THE DRAWINGS

Preferred embodiments of the surgical stapling apparatus of the subject invention will be described in detail hereinbelow with reference to the drawings wherein:

FIG. 2 is a perspective view of a cartridge assembly constructed in accordance with a first embodiment of the subject invention for use with the surgical apparatus of FIG. 1 showing a lockout mechanism in a position wherein the firing shaft has entered the cartridge assembly;

FIG. 4 is an exploded view of the cartridge assembly;

FIG. 5 is a side elevational view in partial cross-section of the cartridge assembly of FIG. 2 showing the approximation shaft in a retracted position and the firing shaft in a pre-fired position;

FIG. 6 is an enlarged side elevational view in cross-section of a portion of the cartridge assembly as illustrated in FIG. 5;

FIG. 7 is a cross-sectional view taken along line 7—7 of FIG. 5;

FIG. 8 is a side elevational view in partial cross-section of the cartridge assembly of FIG. 2 showing the cartridge in an approximated position and the firing shaft in the pre-fired position;

FIG. 16 is a perspective view of the cartridge assembly of FIG. 14 showing the lockout mechanism in a position wherein the firing shaft has entered the cartridge;

FIG. 17 is a perspective view of the cartridge assembly of FIG. 14 showing the lockout mechanism in a post-fired position wherein the firing shaft is prevented from entering the cartridge;

FIG. 18 is an exploded view of the cartridge assembly of FIG. 14;

FIG. 19 is a side elevational view in partial cross-section of the cartridge assembly of FIG. 14 showing the cartridge in an approximated position and the firing shaft in the pre-fired position;

FIG. 20 is a side elevational view in partial cross-section of the cartridge assembly illustrated in FIG. 14 showing the firing shaft in a fired position to drive the staples from the cartridge;

FIG. 21 is an enlarged side elevational view in cross-section of a portion of the cartridge assembly as illustrated in FIG. 20;

FIG. 22 is a side elevational view in partial cross-section of the cartridge assembly of FIG. 14 showing the cartridge in the approximated position, the firing shaft in the retracted position after firing, and the lockout mechanism in a blocking position preventing re-entry of the firing shaft into the cartridge;

FIG. 23 is a side elevational view in partial cross-section of the cartridge assembly illustrated in FIG. 14 showing the approximation shaft in the retracted position, the firing shaft in the retracted position after firing, and the lockout mechanism in a blocking position preventing re-entry of the firing shaft into the cartridge; and FIG. 24 is an enlarged side elevational view in cross-section of a portion of the cartridge assembly as illustrated in FIG. 23.

DETAILED DESCRIPTION OF THE PREFERRED EMBODIMENTS

Figure 3:
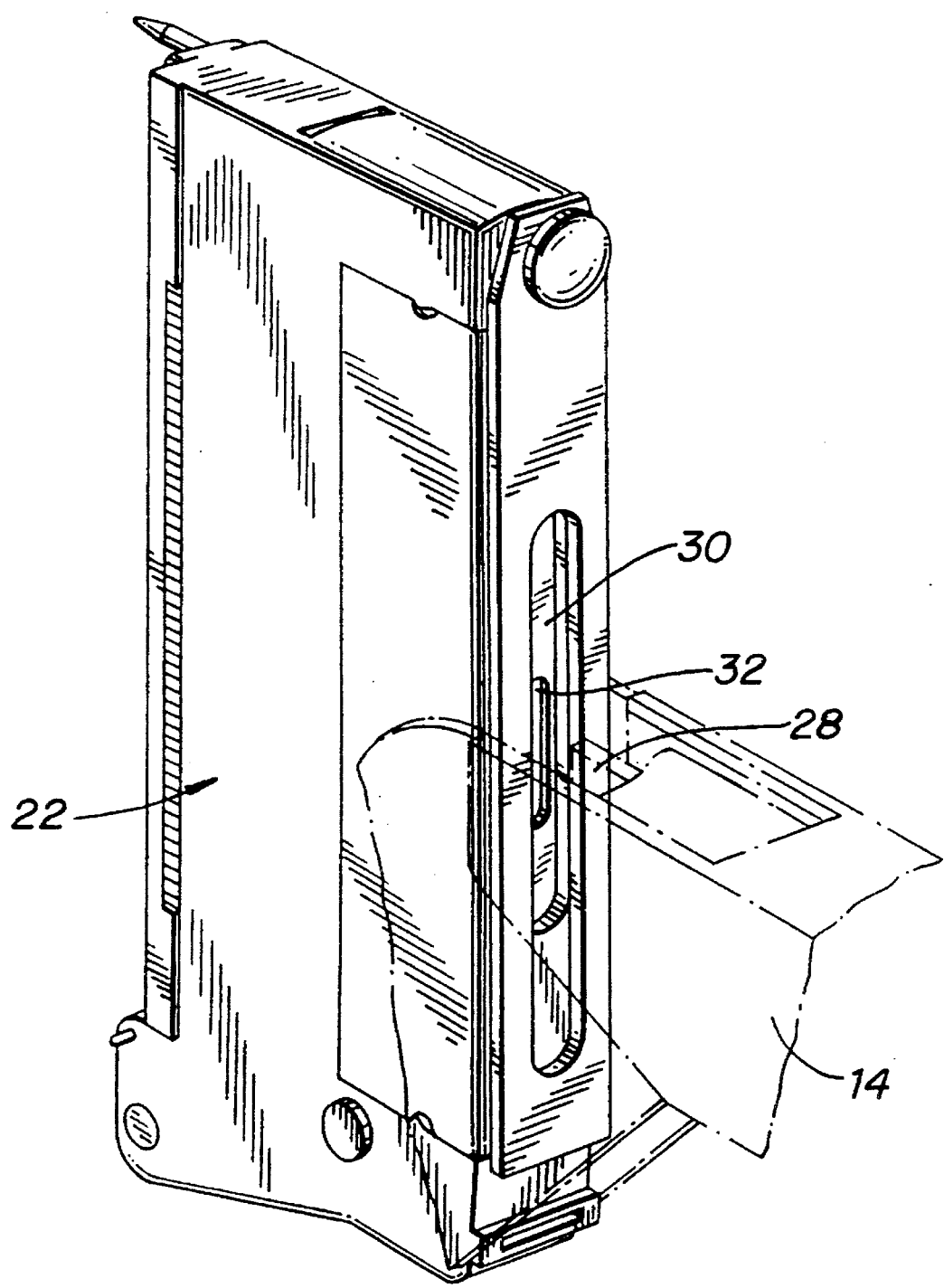
FIG. 3 is a perspective view of the cartridge assembly showing the lockout mechanism disposed in a post-fired position wherein the firing shaft is prevented from entering the cartridge.

In the detailed description which follows, the term "proximal", as is traditional, will refer to the end of the apparatus which is closest to the operator, while the term "distal" will refer to the end of the apparatus which is furthest from the operator. The term longitudinal refers to the direction extending from proximal to distal.

Referring now to the drawings wherein like reference numerals indicate similar structural elements, a surgical stapler constructed in accordance with a preferred embodiment of the subject invention is illustrated and designated generally by reference numeral 10. In brief, surgical stapler 10 comprises a frame 12 having an elongated body 14; a grip portion 16 depending from frame 12; a pivoting actuation handle 18 adjacent grip portion 16; a lower jaw channel positioned at a distal end portion 20 of frame 12 for receiving a staple cartridge 22; an anvil 24 positioned opposite staple cartridge 22 against which staples ejected from cartridge 22 are driven; and an approximation handle 26 pivotably associated with frame 12 for moving cartridge 22 into approximation with anvil 24.

Although described as a staple cartridge for firing staplers for deformation by an anvil, the present invention also contemplates two pan fasteners wherein the fastener portions are positioned in the cartridge and the retainer portions are positioned in the anvil portion of the apparatus. These two pan fasteners can be composed of bioabsorbable material.

Referring to FIGS. 2 and 3, staple cartridge 22, is removably mounted to the stapling apparatus and includes a lockout mechanism for preventing the firing shaft or pusher bar 28 from entering the staple cartridge 22 following a staple firing operation. In general, the lockout mechanism comprises a spring loaded barrier plate 30 having an aperture or slot 32 defined therein to accommodate passage of the firing shaft 28 therethrough during a staple firing operation. Barrier plate 30 is movable from a first position shown in FIG. 3 to permit passage of firing shaft 28 into the cartridge 22 to a second blocking position, illustrated in FIG. 2, following a staple firing operation, after the firing shaft 28 has been retracted from cartridge 22 as described in more detail below.

Positioned within staple cartridge 22 to cooperate with firing shaft 28 for driving the staples is staple 25 driver plate 38 and staple drivers 36 (see FIG. 4). Further illustrations of staple cartridges can be found in U.S. Pat. Nos. 4,568,009 and 4,915,100 incorporated herein by reference. The mechanism for approximating the cartridge as well as the firing mechanism and trigger are conventional and not pan of the present invention. An example of such mechanisms can be found in U.S. Pat. Nos. 4,383,634 and 4,522,327, incorporated herein by reference.

Turning now to FIGS. 5—13, there is illustrated, in sequential order, a staple firing operation during which a plurality of surgical staples 25 are substantially simultaneously ejected from cartridge 22 and applied to tissue 35. Referring initially to FIGS. 5—7, approximation shaft 48 is in a retracted position and staple cartridge 22 is disposed in a non-approximated position spaced from anvil 24 prior to operation of approximation handle 26. Firing shaft 28 is in a pre-fired position outside cartridge 22. Staple cartridge 22 defines an outer casing 34 having substantially parallel side walls which fit within lower channel 20. Staple drivers 36, housed within cartridge 22, each have a plurality of legs 36a for ejecting corresponding staples 25 from cartridge 22 during a staple firing operation, and a staple driver plate 38 which is contacted by firing shaft 28 to advance the staple drivers 36 in a distal direction upon actuation of firing shaft 28.

With continuing reference to FIG. 5, the outer casing 34 of cartridge 22, and in particular, the proximal wall 34a thereof, defines an entryway 40 for accommodating the passage of firing shaft 28 into the cartridge 22. When barrier plate 30 is disposed in a pre-fired position, the aperture 32 formed therein will be aligned with entryway 40 and firing shaft 28 will be permitted to enter cartridge 22. As shown in FIGS. 5 and 6, in the pre-fired position, barrier plate 30 is blocked from movement, i.e. held in place, by port 45 formed in staple driver plate 38, which receives and restrains pin 42 extending distally from barrier plate 30. Barrier plate 30 is normally biased upwardly in the directed of the arrow (FIG. 6) into a post-fired blocking position by a coiled compression spring 44, and is configured to travel in a direction transverse to the direction of travel of firing shaft 28 within a guide track 46 which is illustrated in FIG. 7.

Referring to FIG. 8, staple cartridge 22 is illustrated in approximation with anvil 24. As stated briefly hereinabove, approximation of the staple cartridge 22 and the anvil 24 is achieved through operation of handle 26. More particularly, pivotal movement of approximation handle 26 towards frame 12 drives approximation shaft 48, and associated firing shaft 28, in a distal direction through the body 14 of frame 12. The lip 48a of approximation shaft 48 urges a contact plate 50 and guide pin 52 of the cartridge assembly forward into contact with proximal wall 34a and continues to move cartridge 22 towards anvil 24. Movement of contact plate 50 drives guide pin 52 rewards the anvil, guide pin 52 serving to help entrap tissue between the cartridge 22 and anvil 24. Once contact plate 50 has been moved into an upright position, continued distal translation of the approximation shaft 48 brings cartridge 22 into approximation with anvil 24, as illustrated in FIG. 8.

Figure 9:
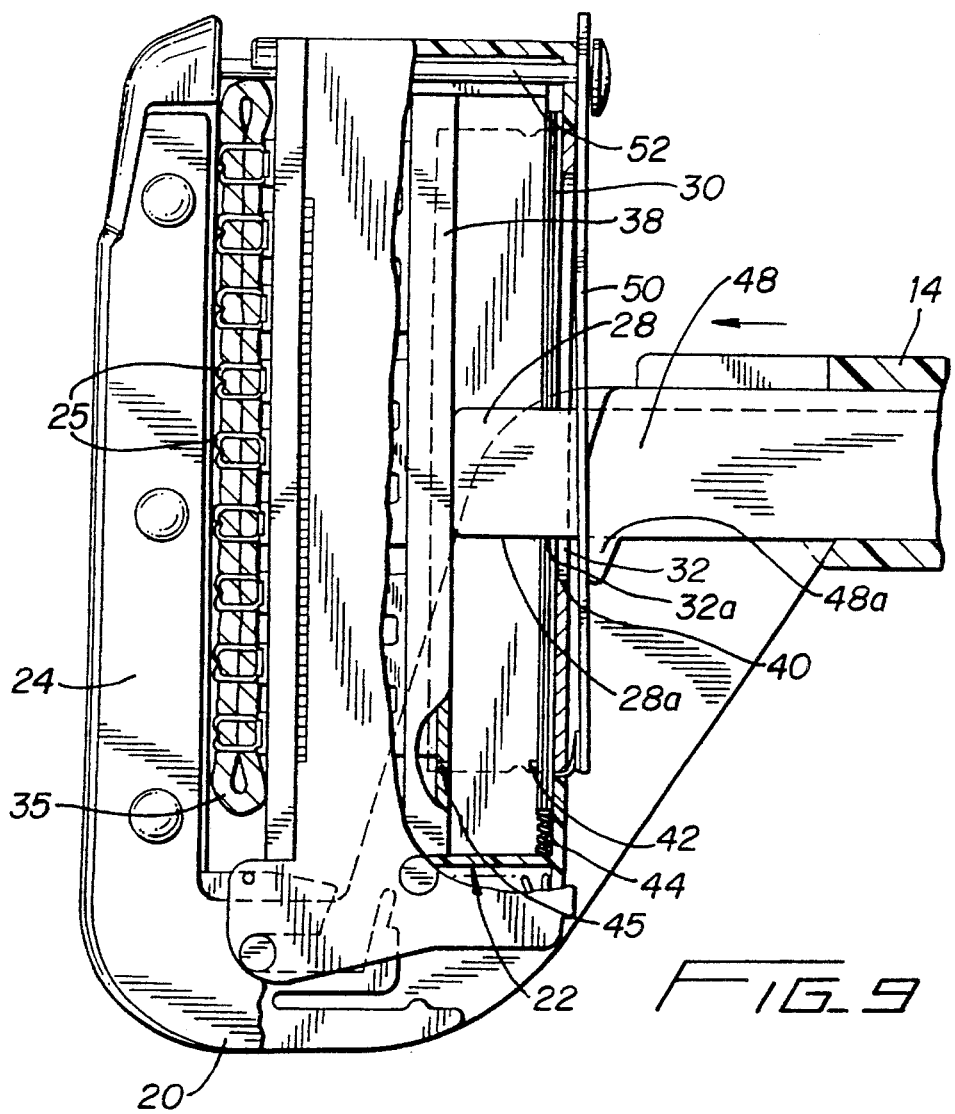
FIG. 9 is a side elevational view in partial cross-section of the cartridge assembly of FIG. 2 showing the firing shaft in a fired position to drive the staples from the cartridge assembly.
Figure 10:
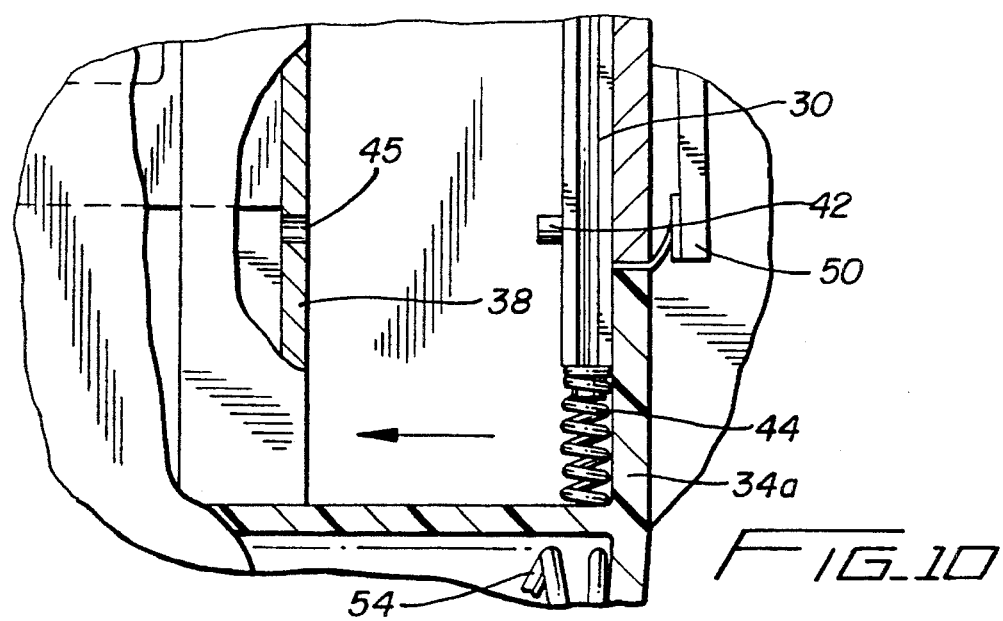
FIG. 10 is an enlarged side elevational view in cross-section of a portion of the cartridge assembly as illustrated in FIG. 9.

Referring to FIGS. 9 and 10, following the approximation of staple cartridge 22 and anvil 24, movement of actuation handle 18 towards grip portion 16 effects the application of staples 25 through tissue 35. Distal longitudinal translation of firing shaft 28 into the cartridge 22 advances staple driver plate 38 distally. As a result, drivers 36 are urged in a distal direction to eject staples 25 from cartridge 22 to be driven through tissue 35 and formed against anvil 24.

When staple driver plate 38 has been advanced distally to fire the staples, the port 45 associated therewith is likewise advanced distally to release the pin 42 which is associated with barrier plate 30. At such a time, barrier plate 30 is no longer restrained by engagement of port 45 and pin 42, and barrier plate 30 is released for movement into a post-fired blocking position under the influence of compression spring 44. However, because the surface 32a of aperture 32 engages bottom 28a of firing shaft 28, barrier plate 30 cannot move into a blocking position until the firing shaft 28 has been retracted from cartridge 22.

Figure 11:
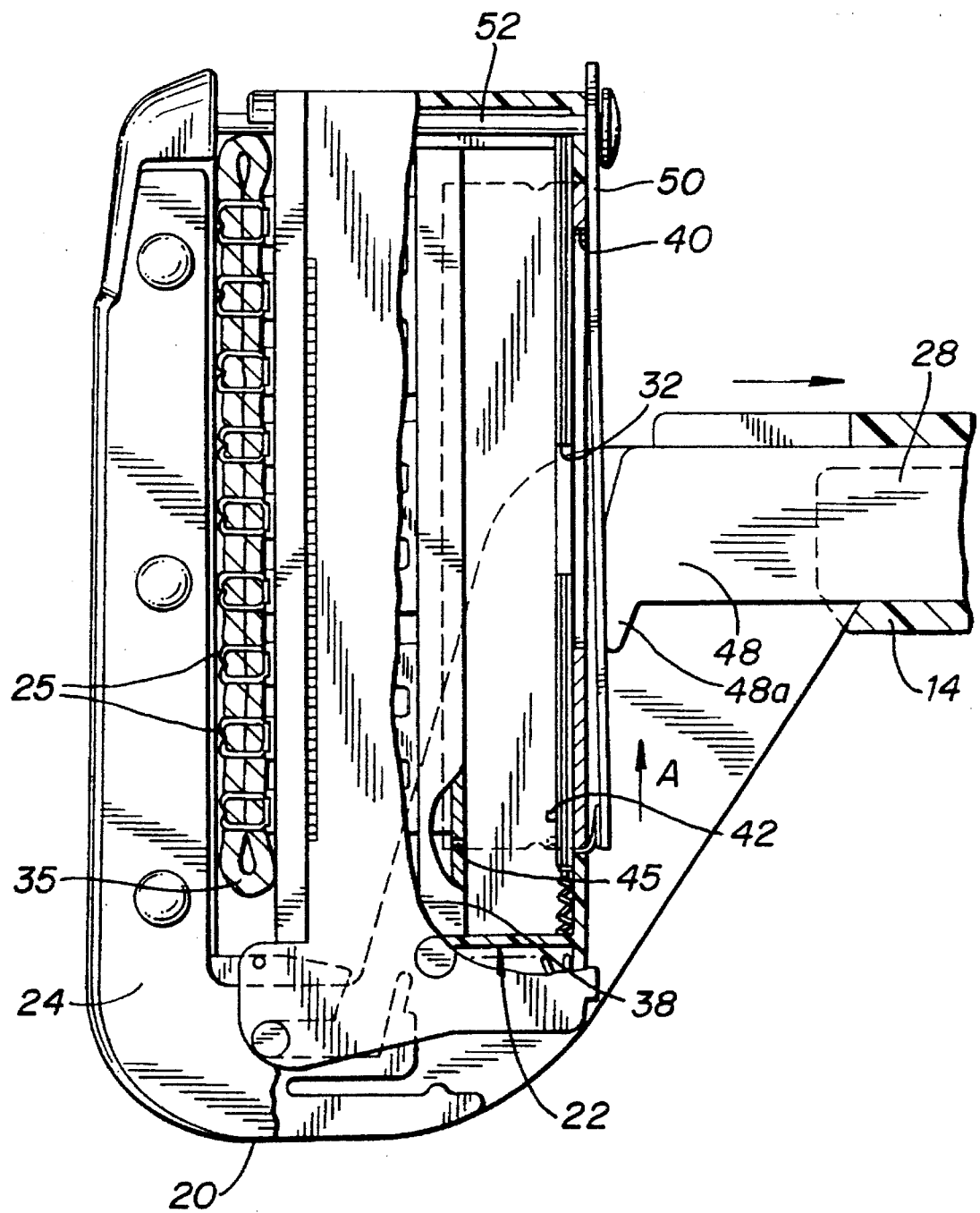
FIG. 11 is a side elevational view in partial cross-section of the cartridge assembly, showing the cartridge in the approximated position, the firing shaft in the retracted position after firing, and the lockout mechanism in a blocking position preventing re-entry of the firing shaft into the cartridge.
Figure 12:
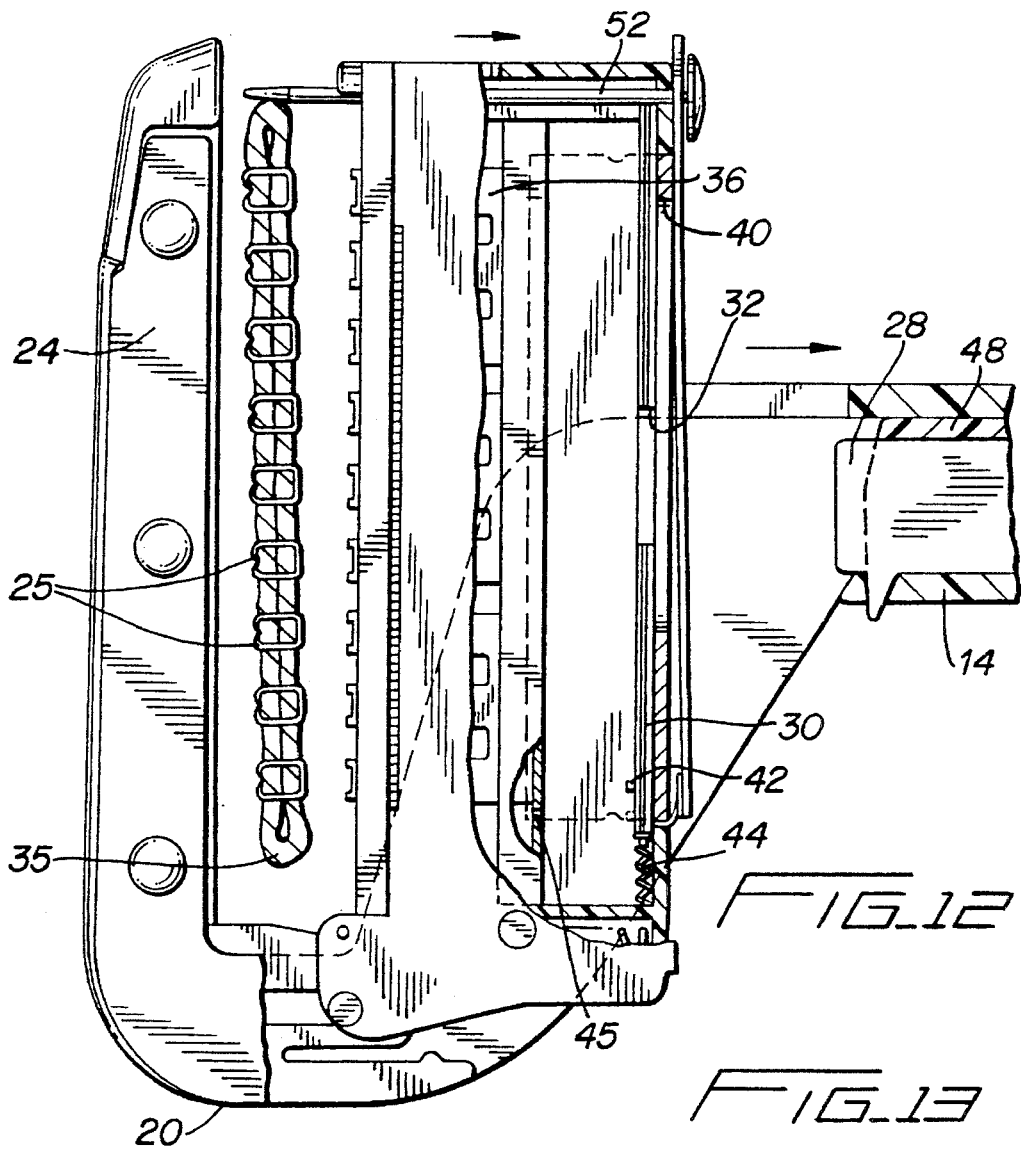
FIG. 12 is a side elevational view in partial cross-section of the cartridge assembly, showing the approximation shaft in the retracted position, the firing shaft in the retracted position after firing, and the lockout mechanism in a blocking position preventing re-entry of the firing shaft into the cartridge.
Figure 13:
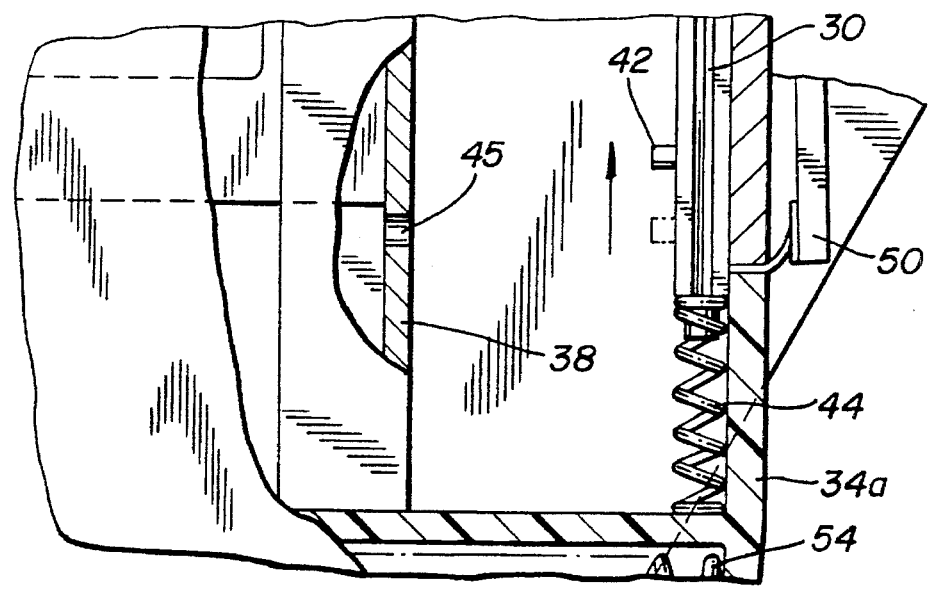
FIG. 13 is an enlarged side elevational view in cross-section of a portion of the cartridge assembly as illustrated in FIG. 12.

Referring to FIG. 11, upon release of actuation handle 18, firing shaft 28 moves proximally, i.e., in a direction opposite the movement of the firing shaft 28 to fire the staples, to its retracted prefired position. As shown, this allows spring loaded barrier plate 30 to move into a blocking position (in the direction of the arrow A) transverse to the direction of movement of firing shaft 28, under the influence of compression spring 44. At such time, at least part of the is aperture 32 which is formed in barrier plate 30 is out of alignment with the entryway 40 formed in the proximal wall 34a of cartridge casing 34. (see also FIG. 3.) Thus, a solid portion of barrier plate 30 will project into the path of firing shaft 28. When approximation lever 26 is released, approximation shaft 48 returns to its retracted position and the staple cartridge 22 translates in a proximal direction under the influence of a coiled return spring 54. This position is illustrated in FIG. 12.

As a result of this movement of barrier plate 30, firing shaft 28 is blocked and prohibited from entering staple cartridge 22 through aperture 32. Consequently, surgical stapler 10 cannot be operated again until the spent cartridge from which the fasteners have been ejected has been removed from the stapler and a new fully loaded cartridge has been placed into the stapler. Furthermore, if, by chance, the surgeon or nurse utilizing the instrument accidentally inserts a spent cartridge into the stapler, barrier plate 30 will prohibit such inadvertent use because a solid portion of the barrier plate 30 will be in alignment with the portion of the cartridge casing entryway 40 through which firing shaft 28 travels and firing shaft 28 will be blocked from moving in a firing path through the aperture and into the cartridge. It is also envisioned that barrier plate 30 can serve as a visual indicator to alert a user that a particular staple cartridge is either loaded with staples, or that the staples once contained therein have been ejected.

Referring now to FIGS. 14–24, another staple cartridge constructed in accordance with an alternate embodiment of the subject invention is illustrated and designated generally by reference numeral 122. Staple cartridge 122 received at a distal end portion 120 of the frame, is substantially identical, in both structure and function, to the staple cartridge 22 which has been described hereinabove, except that cartridge 122 contains a different lockout mechanism. In particular, the lockout mechanism comprises a spring loaded barrier wall 130 instead of the barrier plate 30 provided in staple cartridge 22 described above. Barrier wall 130, as will be described below, is movable from a position below the path of the firing shaft 128 to a position within the path of firing shaft 128.

Barrier wall 130 is movable from a prefired position (FIG. 16) into a blocking position as illustrated in FIG. 17 upon retraction of the firing shaft 128 from cartridge 122 after the staples 125 have been fired. In a blocking position, barrier wall 130 prohibits the passage of firing shaft 128 through the entryway 140 defined in the proximal wall 134a of the outer casing 134 of cartridge 122 following a staple firing operation.

Figure 14:
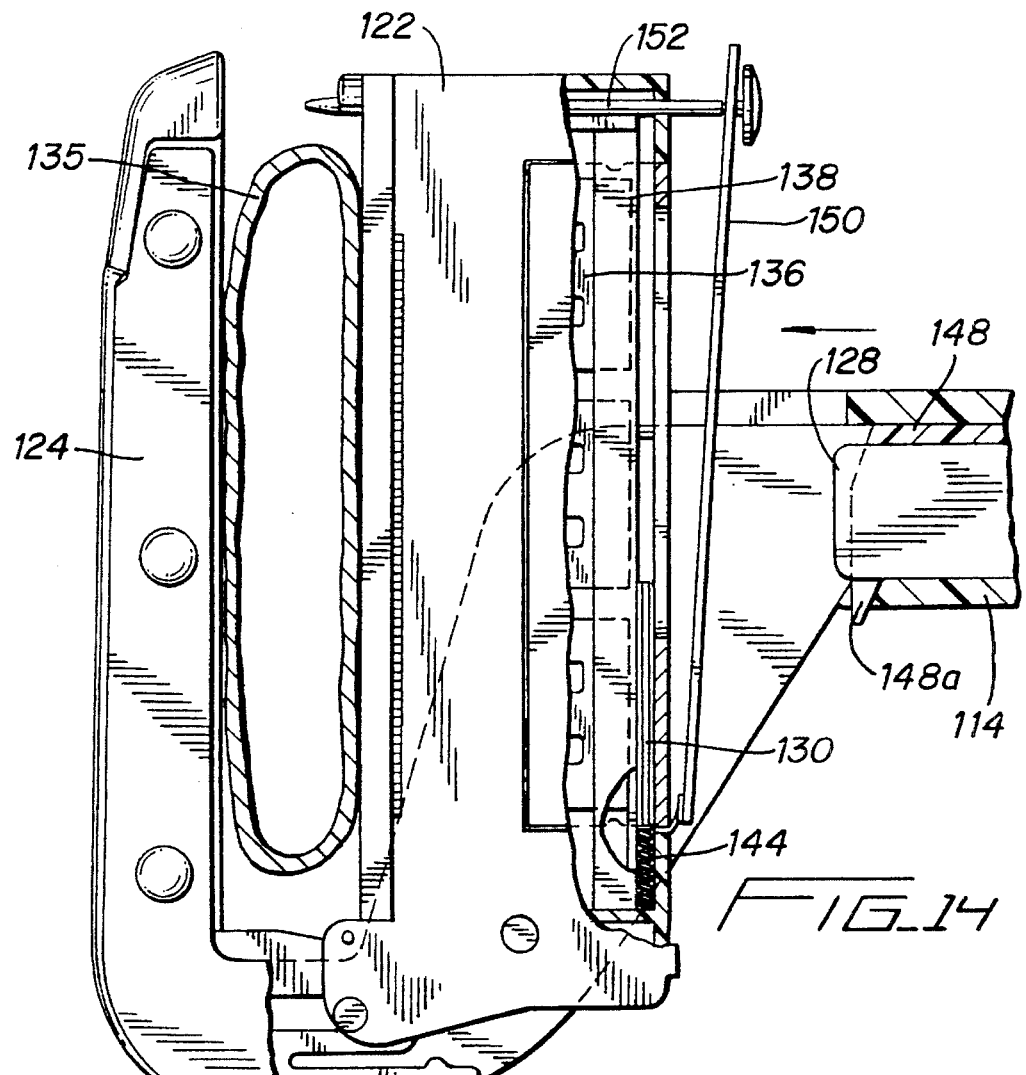
FIG. 14 is a side elevational view in partial cross-section of the cartridge assembly constructed in accordance with another embodiment of the subject invention showing the approximation shaft in a retracted position and the firing shaft in a pre-fired position.
Figure 15:
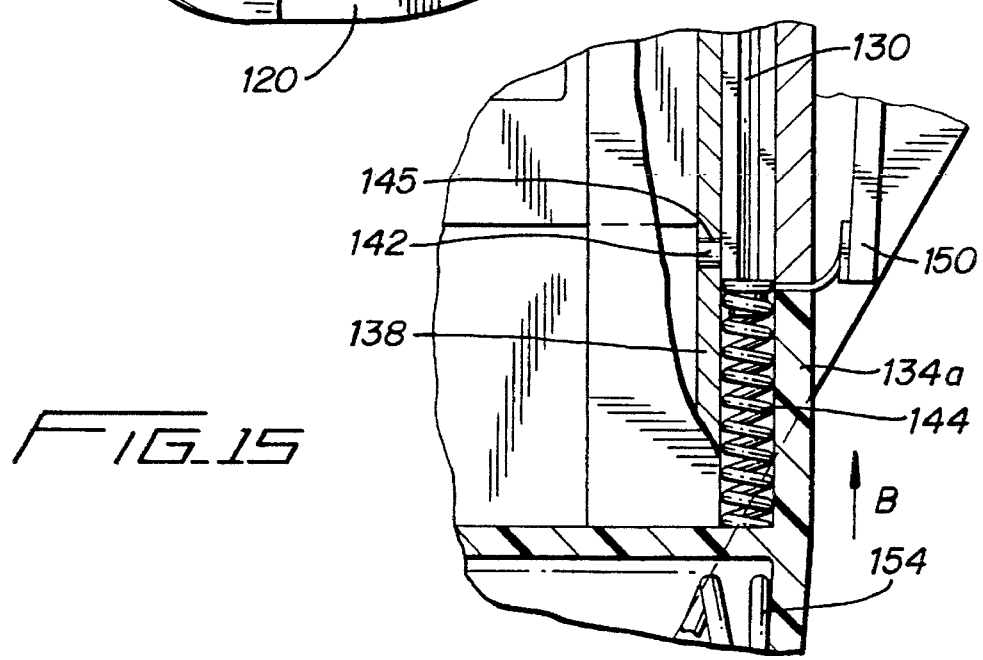
FIG. 15 is an enlarged side elevational view in cross-section of a portion of the cartridge assembly as illustrated in FIG. 14.
Figure 1B:
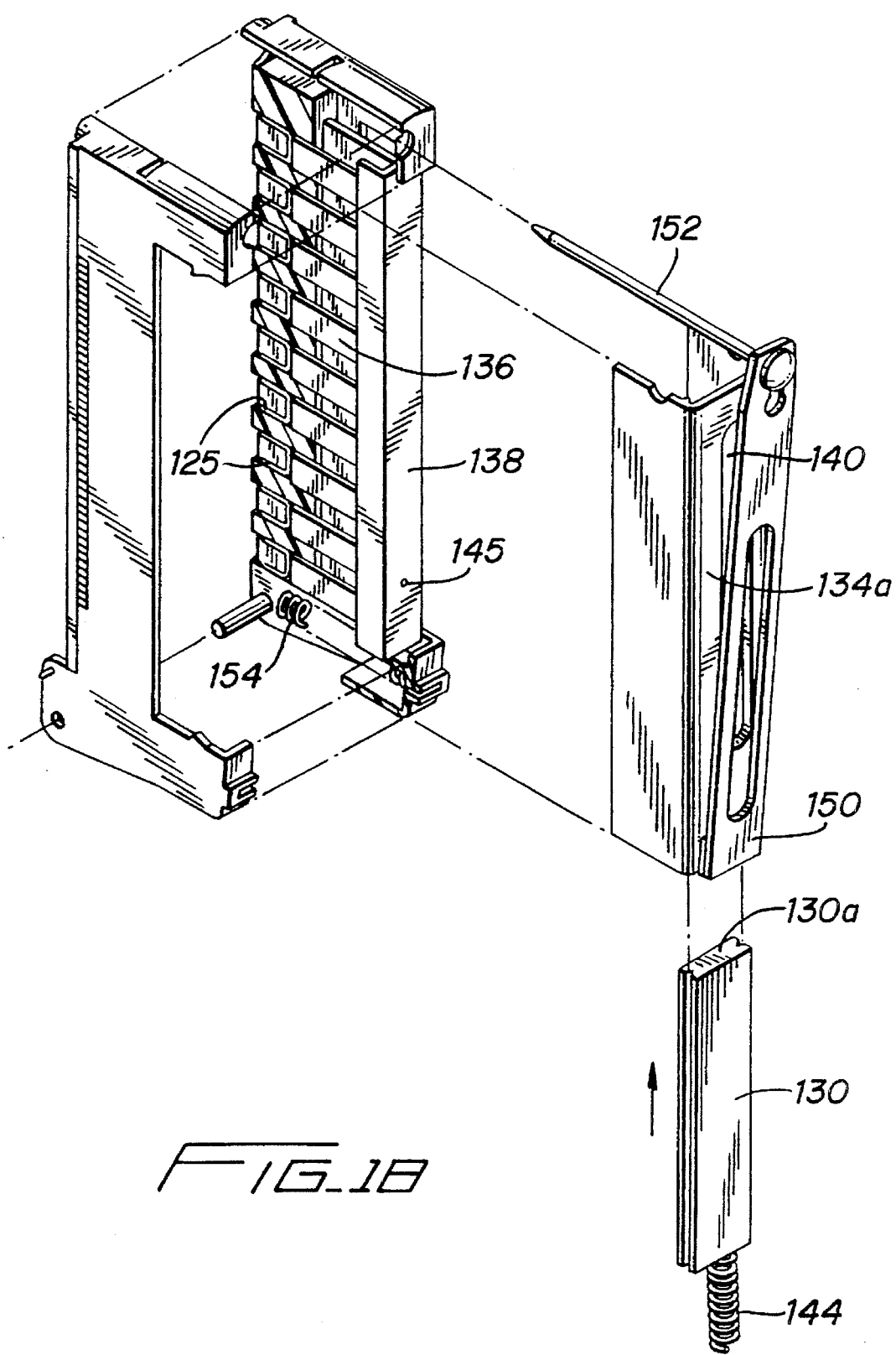
FIG. 1 is a perspective view of the surgical stapling apparatus of the subject invention.

Turning now to FIGS. 14, 15 and 19–24, there is illustrated, in sequential order, a staple firing operation similar to that described hereinabove and illustrated in FIGS. 5–13. Referring initially to FIGS. 14 and 15, the staple cartridge 122 is disposed in a non-approximated position spaced from anvil 124 prior to operation of stapler 10. At such a time, as best seen in FIG. 15, the barrier wall 130 is blocked from movement by reception port 145 formed in staple driver plate 138 which receives and restrains pin 142 extending from barrier wall 130. Thus, the firing path is clear for firing shaft 128. A coiled compression spring 144 biases barrier wall 130 into the post-fired blocking position upwardly in the direction of arrow B.

Referring to FIG. 19, cartridge 122 is illustrated in approximation with anvil 124 by the distal translation of approximation shaft 148 (and lip 148a) in response to operation of handle 26 in a similar manner as described above with respect to the first embodiment. That is, approximation shaft 148 moves in a distal direction through the body 114 of the frame such that lip 148a urges contact plate 150 and guide pin 152 forward to move the cartridge 122 towards anvil 124, compressing return spring 154. Following approximation of cartridge 122, the stapler may be operated to apply a plurality of surgical fasteners 125 to the tissue 135 disposed between the cartridge 122 and anvil 124.

Referring to FIGS. 20 and 21, distal translation of firing shaft 128 in response to operation of the actuation handle 16 advances staple driver plate 138 in a distal direction. As a result, staple drivers 136 are urged distally to eject surgical staples 125 from cartridge 122. When staple driver plate 138 has been advanced distally, the pin 142 extending from barrier wall 130 is no longer engaged by the reception port 145. At such a time, barrier wall 130 is released for movement into a blocking position under the bias of compression spring 144, however its movement is restricted by the presence of firing shaft 128 within cartridge 122. That is, surface 130a of barrier wall 130 abuts bottom surface 128a of firing shaft 128.

Referring to FIGS. 22–24, when the firing shaft 128 is retracted from staple cartridge 122, the barrier wall 130 moves in the direction of the arrow C into a blocking position under the influence of compression spring 144. At such a time, barrier wall 130 blocks the entryway 140 formed in the proximal wall 134a of cartridge casing 134. As a result, firing shaft 128 is prohibited from entering staple cartridge 122 and surgical apparatus 10 is rendered inoperative until such time as the spent staple cartridge is removed and replaced with a new fully loaded staple cartridge.

Although the surgical stapler of the subject invention has been described with respect to a preferred embodiment, it will be readily apparent to those having ordinary skill in the art to which it appertains that changes and/or modifications may be made thereto without departing from the spirit or scope of the subject invention as defined by the appended claim.

What is claimed is:

1. A surgical stapler comprising:

a frame having a longitudinal axis and a cartridge receiving portion;

an anvil portion positioned at a distal end of said frame;

a cartridge containing a plurality of fasteners, a plurality of fastener drivers and a fastener driving plate positioned proximally of said fastener drivers, said cartridge mountable in said cartridge receiving portion;

means for moving said cartridge between a proximal first position and a distal second position closer to said anvil portion;

means for substantially simultaneously firing said fasteners from said cartridge in a direction substantially parallel to said longitudinal axis, said firing means including a firing shaft and said fastener driving plate;

a slidable plate positioned in said cartridge proximally of said fastener drivers and substantially perpendicular to said longitudinal axis, said slidable plate being spring biased towards said firing shaft;

an elongated aperture formed in said slidable plate and dimensioned and configured to allow passage of said firing shaft therethrough to fire said fasteners; and a retaining pin extending from said slidable plate for reception in an opening in said fastener driving plate, said slidable plate being movable from a first position wherein said retaining pin is positioned in said opening to a second position wherein said retaining pin is released from said opening, said slidable plate movable to said second position after distal movement of said firing shaft and said driving plate to fire said fasteners and retraction of said firing shaft, wherein in said second position at least a portion of said elongated aperture of said slidable plate is out of alignment with said firing shaft such that passage of said firing shaft is prevented by said slidable plate.

2. A surgical stapler according to claim 1, further comprising a spring positioned in said cartridge for biasing said slidable plate towards said firing shaft.

3. A surgical stapler according to claim 2, wherein said opening is formed in an intermediate portion of said driving plate.

* * * * *